United States Patent
Hughes et al.

(10) Patent No.: US 10,132,906 B2
(45) Date of Patent: Nov. 20, 2018

(54) MULTI-ELEMENT SENSOR ARRAY CALIBRATION METHOD

(71) Applicant: ROLLS-ROYCE plc, London (GB)

(72) Inventors: Robert R Hughes, Bristol (GB); Christopher J L Lane, Singapore (SG)

(73) Assignee: ROLLS-ROYCE plc, London (GB)

( * ) Notice: Subject to any disclaimer, the term of this patent is extended or adjusted under 35 U.S.C. 154(b) by 36 days.

(21) Appl. No.: 15/235,764

(22) Filed: Aug. 12, 2016

(65) Prior Publication Data

US 2017/0059683 A1 Mar. 2, 2017

(30) Foreign Application Priority Data

Sep. 1, 2015 (GB) .................................. 1515483.4

(51) Int. Cl.
*G01R 35/00* (2006.01)
*G01D 18/00* (2006.01)
*G01N 27/90* (2006.01)

(52) U.S. Cl.
CPC ......... *G01R 35/005* (2013.01); *G01D 18/008* (2013.01); *G01N 27/9086* (2013.01)

(58) Field of Classification Search
CPC . G01R 35/005; G01D 18/008; G01N 27/9086
See application file for complete search history.

(56) References Cited

U.S. PATENT DOCUMENTS 6,252,393 B1 * 6/2001 Hedengren .......... G01B 21/042
324/202
6,933,718 B2 8/2005 Collingwood et al.
2010/0312494 A1 * 12/2010 Korukonda .......... G01N 27/904
702/38
2014/0091784 A1 4/2014 Raulerson et al.

FOREIGN PATENT DOCUMENTS

DE  11 2007 003 747 T5   12/2010
EP    0 969 267 A1        1/2000

OTHER PUBLICATIONS

Apr. 6, 2016 Search Report issued in British Patent Application No. 1515483.4.

(Continued)

*Primary Examiner* — Huy Q Phan
*Assistant Examiner* — Zannatul Ferdous
(74) *Attorney, Agent, or Firm* — Oliff PLC

(57) ABSTRACT

A method of calibrating a sensor array having elements spaced from one another in a first direction, the array defining an array spatial response function, includes: providing a test workpiece having at least first and second calibrated defects spaced apart in the first direction by a characteristic distance such that when the first calibrated surface defect is located at a position corresponding to an array response function maximum, the second calibrated surface defect is located at a position corresponding to an array response function minimum; passing the array across the first and second calibrated surface defects in a direction normal to the first direction and determining a peak sensor signal from at least two of the elements in the array to determine an array spatial response function root mean squared average; and setting a rejection threshold as a predetermined proportion of the array spatial response function root mean squared average.

8 Claims, 5 Drawing Sheets

(56) References Cited

OTHER PUBLICATIONS

"Eddy Current Array Technology—Chapter (8): Array Signal Calibration", Fundamentals & Applications for Non-Destructive Testing, Eclipse Scientific 1st Edition, pp. 127-139.
Jan. 25, 2017 Search Report issued in European Patent Application No. EP 16 18 4005.

* cited by examiner

MULTI-ELEMENT SENSOR ARRAY CALIBRATION METHOD

FIELD OF THE INVENTION

The present invention relates to a method of calibrating a multi-element sensor array such as an eddy current array (ECA).

BACKGROUND TO THE INVENTION

FIG. 1 illustrates the working principle of an eddy current inspection device for inspecting an electrically conductive workpiece 4. The device operates by flowing a primary electrical current through a sensor comprising a coil of wire 1 to induce a primary magnetic field indicated by 2. The primary magnetic field 2 in turn induces a secondary electrical field 3 in an adjacent conductive (e.g. metallic) workpiece 4 to be inspected. The secondary electrical field 3 in turn induces a secondary magnetic field 5, which interacts with the primary electrical current flowing through the coil 1. The change in electrical current in the coil 1 can be detected by measuring one or more of the impedance (Z), magnitude (|Z|) and phase (φ) of the current I and/or voltage V flowing through the coil 1, to thereby deduce the properties of the workpiece 4 near the surface. This change can be detected using equipment such as an ammeter, voltmeter or oscilloscope. For example, small defects at or near the surface will result in a reduced or increased impedance, magnitude or phase of the current relative to other areas.

The surface of the workpiece 4 can be inspected by rastering the sensor 1 across the surface, and measuring the electrical properties of the current in the coil as the device is passed along the surface. However, such a method is relatively slow.

One alternative is to provide an array of sensors. FIG. 2 shows one such array 10, which comprises nine sensors 12 arranged in first and second rows. Each sensor 12 comprises a coil of wire similar to that shown in FIG. 1, which is independently supplied with electrical current. A centre of the coil of each sensor 12 is spaced a distance $d_2$ from the centre of an adjacent sensor coil in the next row, with the rows being spaced, and with the rows being staggered such that the centre of the sensor 12 in the first row is located mid-way between the sensors 12 in the second row at a resolution better than the physical size of the sensors 12 in view of the staggered rows. By moving this array 10 in a single direction X normal to the row orientation, a large area of the workpiece 4 can be scanned at once by monitoring the signals produced by each sensor 12, thereby reducing the time required to perform a scan. However, such arrays generally have a lower sensitivity and a lower resolution compared to rastered single sensors, which is limited by the spacing $d_2$ in the example shown in FIG. 2. Such arrays also have a lower signal to noise ratio in view of the proximity of the adjacent sensors 12, and so must be carefully normalised and calibrated to identify the correct threshold for rejection. Such calibration generally has to be repeated frequently, and can account for a large proportion of total testing time.

One calibration method is to provide an electrically conductive test article having a surface similar to the component to be inspected, having a single defect comprising a calibration notch of known dimensions, and passing the array along the test article, past the notch at position p. The signal is monitored, and a threshold set accordingly. FIG. 3 shows a graph illustrating a signal magnitude (such as phase, amplitude or impedance) of a single sensor 12 of the array 10 as it passes the notch p. The gain of the monitoring device is adjusted such that the screen height is approximately 80% of the maximum signal (so that the monitor is not saturated in use), and a rejection threshold is set at, for example, 30% of the screen height (which has been found to be sufficiently greater than the signal to noise ratio for most cases). Such a method is described for example in Chapter 8 of "Eddy Current Array Technology", published by Eclipse scientific.

However, it has been found that such calibration methods may result in some defects going undetected. For example, if the length of the defect normal to the direction X is less than the sensor spacing $d_2$, the peak signal from any one sensor 10 may be less than the rejection threshold, and in such cases, the workpiece would be accepted despite having a defect. In order to improve the accuracy of the rejection threshold, multiple passes must be made, with the array being slightly repositioned for each pass. Consequently, such calibration methods are time consuming. Similar problems also occur in other multi-element sensor arrays.

EP0969267 describes an alternative method and apparatus for calibrating a prior method of calibrating an eddy current sensor array. The method comprises providing a metallic plate having a plurality of spaced notches and passing the sensors array across the notches. However, generally, more than one pass is required in order to fully calibrate the array.

The present invention describes a method of calibrating an eddy current array inspection device which seeks to overcome some or all of the above problems.

SUMMARY OF THE INVENTION

According to a first aspect of the present disclosure, there is provided a method of calibrating a sensor array, the array comprising a plurality of sensor elements spaced from one another in a first direction, the array defining an array spatial response function, the calibration method comprising the following steps:

providing a test workpiece comprising at least first and second calibrated defects spaced apart in the first direction by a characteristic distance such that when the first calibrated defect is located at a position corresponding to a maximum of the array response function, the second calibrated defect is located at a position corresponding to a minimum of the array response function;

passing the array across the first and second calibrated defects in a direction normal to the first direction and determining a peak sensor signal from at least two of the sensor elements in the array to determine a root mean squared average of the array spatial response function; and setting a rejection threshold as a predetermined proportion of the root mean squared average of the array spatial response function.

It has been found by the inventors that a rejection threshold based on the root mean squared average (RMS) of an array spatial response function provides a more reliable rejection threshold than the prior art method. It has also been found that an approximation for the RMS value of the array spatial response function can be found from a single pass of the array by providing at least a pair of calibrated defects arranged such that, when one calibrated defect is located at the peak of the array response function, the other is at the minimum. Consequently, the variations in sensor signals from sensor elements at different positions in the array is cancelled out, such that the RMS average of the array function as a whole can be calculated using signals generated by these calibrated defects.

The array may comprise an eddy current sensor array. Alternatively, the array may comprise other magnetic field sensors, for example Giant Magnetoresistance (GMR) sensors or Hall Effect sensors.

Each of the first and second calibrated defects may comprise an indentation in a surface of the test workpiece, and may define a length in the first direction of 0.75 mm, a width parallel to the surface of the component and normal to the first direction of 0.38 mm, and a depth of 0.1 mm. The length of each calibrated defect in the first direction may be less than half a channel width $\phi$ of the sensor elements. A centre of each of the first and second surface calibrated defects may be spaced apart a distance 1.5n times a sensor element channel width $\phi$, where n is a positive integer. It has been found that this distance corresponds to the maximum and minimum of the array response function for arrays having equally spaced sensors.

The sensor array inspection device may comprise first and second rows of sensor elements, each row being spaced from the adjacent row in a direction normal to the first direction.

The sensor elements of the first and second rows may be staggered such that a centre of a sensor element of a first row may be located equidistant from a pair of sensor elements in the second row.

The test workpiece may comprise further calibrated defects spaced apart from one another by the characteristic distance.

The step of calculating the root mean squared of the array spatial response function may comprise calculating an average of the determined peak sensor signals from a plurality of sensor elements in the array passing each of the calibrated defects.

Alternatively, the step of calculating the root mean squared average of the array spatial response function may comprise determining a ratio of peak sensor signals from adjacent sensor elements in the array when each passes over a first notch;

determining a position of the first notch relative to the array spatial response function using the ratio of peak sensor signals;

determining a first gradient by dividing the ratio by the channel width;

drawing first and second notional lines reflected about the first notch position, the first notional line having the determined gradient, the second notional line having the magnitude of the determined gradient and opposite sign;

determining a plurality of candidate array spatial response function points having positions along the first and second lines;

fitting a candidate function to the candidate array special response function points; and calculating a mean squared average of the candidate function.

DETAILED DESCRIPTION

Figure 4:
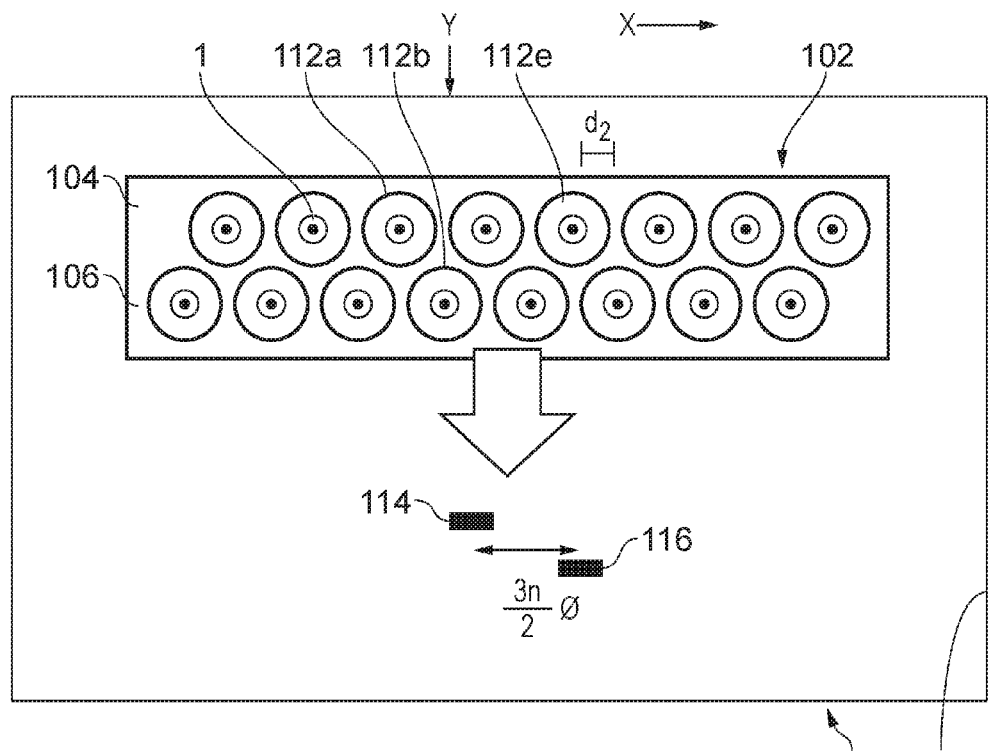
FIG. 4 shows a schematic plan view of a first eddy current array calibration apparatus in accordance with the present disclosure.

FIG. 4 shows an eddy current array inspection device calibration apparatus 100. The apparatus 100 comprises an eddy current array inspection device 102 and a calibration block 110.

Figure 1:
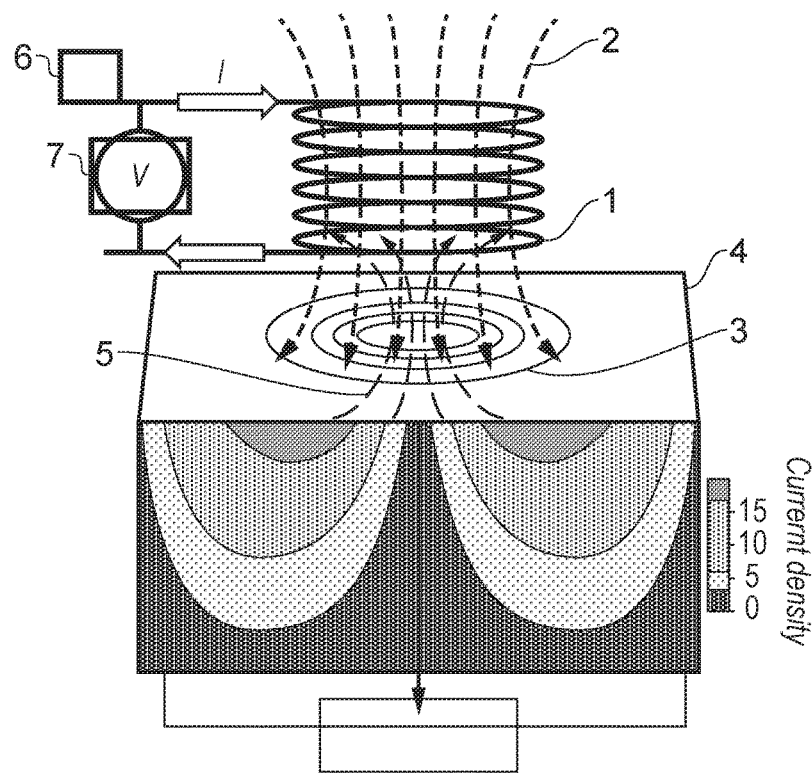
FIG. 1 shows a schematic of a sensor element of an eddy current inspection device in accordance with the present disclosure.
Figure 2:
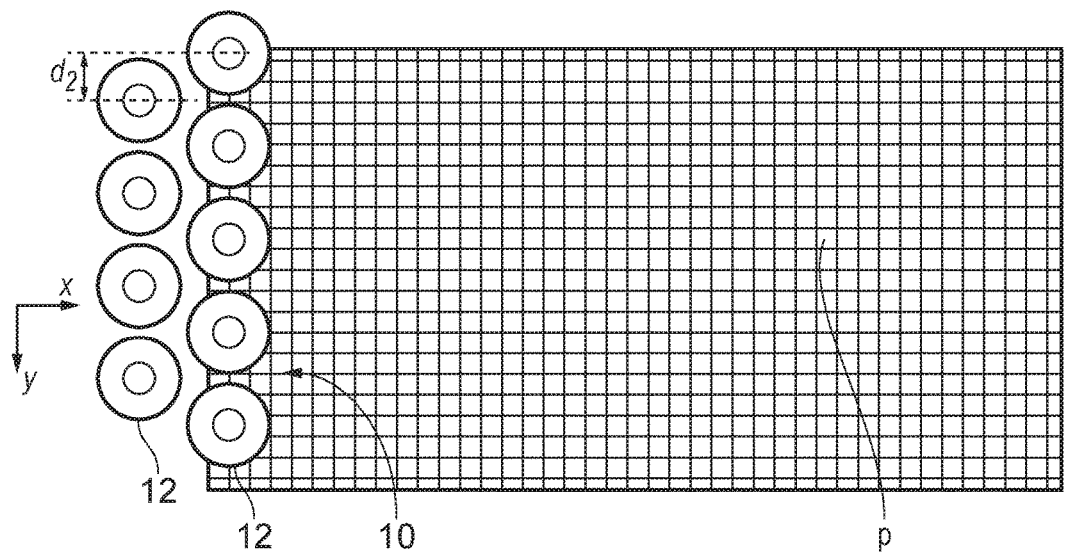
FIG. 2 shows a plan view of an eddy current array inspection device in accordance with the present disclosure having the sensor element of FIG. 1.
Figure 3:
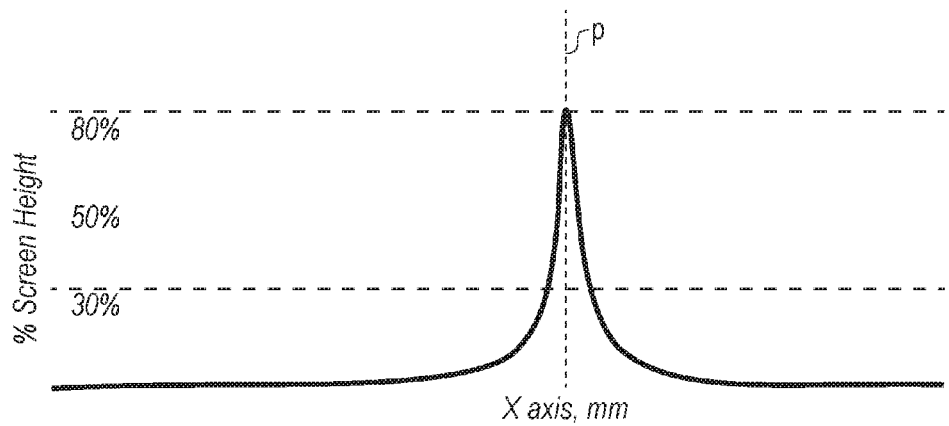
FIG. 3 illustrates a prior method of calibrating an eddy current array inspection device.

The inspection device 102 comprises a plurality of sensor elements 112. Each sensor element 112 comprises an electromagnetic coil 1 (shown in further detail in FIG. 1), which is connected to a power source 7 and an electrical current sensor 6, which detects at least one of the impedance (Z), magnitude (|Z|) and phase ($\varphi$) of the current I flowing through the coil 1, to thereby detect near surface defects in an electrically conductive article comprising, for instance, a metal or a carbon fibre composite.

The coils 1 of the sensors 112 of the inspection device 102 are spaced apart in rows 104, 106 extending in a direction X to define an array. The array further defines a direction Y normal to the direction X, parallel to the surface of the calibration block in use. Each row 104, 106 is staggered, such that a centre of coils 1 within a first row 104 are located equidistant from adjacent coils in an adjacent second row 106. A centre of each coil 1 is spaced from an adjacent coil 1 in the array along the direction x by a distance $d_2$. Each sensor element in the array defines a channel width $\phi$, which in this case is the distance $d_2$ between centres of each coil 2. More generally, the channel width is $\phi$ the width between minima of the array response function, described in further detail below.

The calibration block 110 comprises an electrically conductive material similar to that which the inspection device is configured to inspect, such as steel. The block comprises at least first 114 and second 116 calibrated near surface defects in the form of indentations into a surface of the calibration block 110. The indentations 114, 116 are each 0.75 mm long in the x direction, 0.38 mm wide normal to the x direction, and 0.1 mm deep into the surface of the calibration block. These dimensions are chosen such that the calibrated defect is of a minimum size that the inspection device is configured to detect. The centres of the first and second indentations 114, 116 are spaced apart in the x direction a distance equal to an integer multiple of 1.5 times the channel width $\phi$, for reasons that will be made clear. The first and second indentations 114, 116 are also staggered in the Y direction to avoid interference between signals from the first and second indentations 114, 116.

Figure 5:
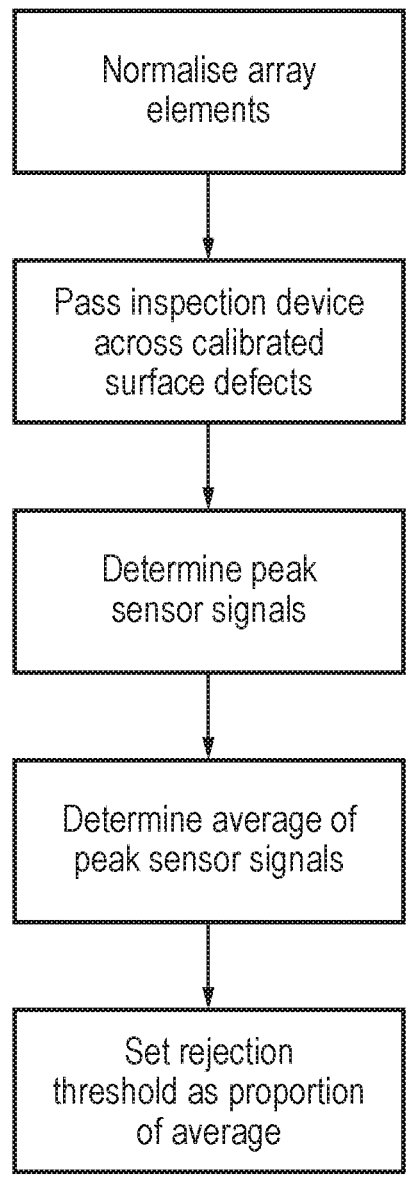
FIG. 5 is a flow diagram illustrating a first method of calibrating an eddy current array inspection device in accordance with the present disclosure.

Referring to FIG. 5, a method of calibrating the inspection device 102 using the apparatus 100 is described. In calibration, a sensor reading is correlated with a defect magnitude, so that a given sensor reading can be used to determine the corresponding sensed defect magnitude in use.

In a first step prior to calibration process, the elements 112 in the array 102 are normalised, such that the same sensor reading is provided by each element 112 in the array for a given defect. This may involve passing the elements in the array 102 over a slot extending in a direction parallel to the first direction, such that each of the elements detect a similar slot at the same time. The sensing equipment is then adjusted such that each of the elements is normalised, i.e. measures the same magnitude for the normalisation slot.

In a first calibration step, with the coils 1 energised, the inspection device 102 is passed along the calibrated defects 114, 116 in the direction X. As the device 102 is passed over the defects, a signal from the sensor elements in the array (e.g. current impedance, magnitude and phase) is monitored, and the two highest magnitude peak signal values from separate sensors are recorded in a second step. These two peak sensor values correspond to sensor readings as the sensor elements 112 pass over the defects. The peak sensor values will be from the monitored sensor elements 112 having the highest peak reading, which will correspond to the sensor elements 112b and 112e in the array which are closest to the indentations 114, 116 respectively in the example shown in FIG. 4.

In a third step, the peak signal values of the sensor elements 112 determined in the second step are averaged to provide an averaged sensor value. This averaged sensor value represents an approximation of the Root Mean Squared (RMS) value of the array response function. Screen height (i.e. maximum sensitivity of the electrical current sensor 6, which could for instance comprise an oscilloscope) is set at 80% of the averaged sensor value. In a fourth step, the rejection threshold for the array is set at a proportion of this averaged sensor value, for example, 30% of screen height.

It has been found that the calibration method of the present invention can provide a rejection threshold which is high enough to ensure that signal noise does not provide false detections of non-existent defects, whilst being low enough to detect defects at the limit of the sensor array resolution, while requiring only a single sensor pass. Consequently, inspection device accuracy is increased, while setup time is reduced.

Figure 6:
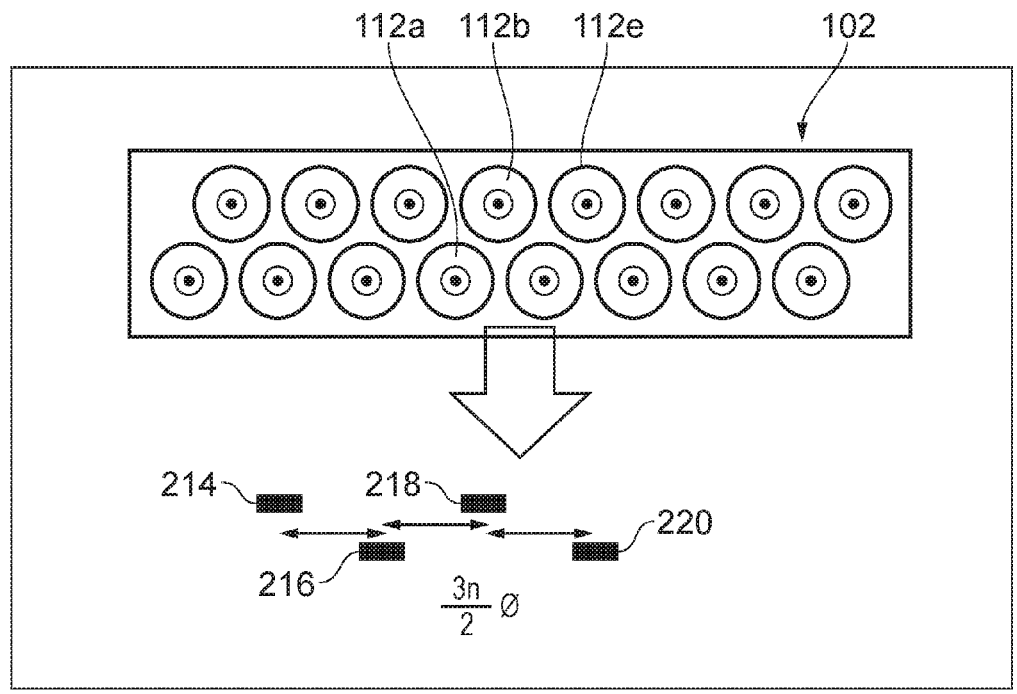
FIG. 6 is a plan view of a second eddy current array calibration apparatus in accordance with the present disclosure.

The above method is thought to work, since the array defines an "array response function", i.e. a relationship between the magnitude of the signal from the normalised sensor elements of the array, and position in the X direction. In general, this array response signal is of the form $f(x)=A\sin^2(x)$, where x represents the position in the X direction, and y represents the magnitude of the signal for a given sized defect at position X. A graph of an example array response function is shown in FIG. 6. As can be seen, a number of characteristic points on the curve can be identified. These include a position in the X direction having a maximum signal amplitude $x_{max}$ and a position in the X direction having a minimum signal amplitude $x_{min}$. The distance in the X direction between successive array response function minima $x_{min}$ represents half the channel width $\phi/2$.

FIG. 6 shows a second calibration apparatus 200 of the present disclosure. The apparatus 200 is similar to the apparatus 100 using the same an inspection device 102 and a similar calibration block 210, but in this case, the calibration block 210 comprises four calibrated defects 214, 216, 218, 220 instead of two. Again, the defects 214-220 are separated in the X direction by an integer multiple of 1.5 times the channel width $\phi$. In this case, the increased number of calibrated defects potentially permits a more accurate estimation of the RMS of the spatial response function of the array.

Figure 7:
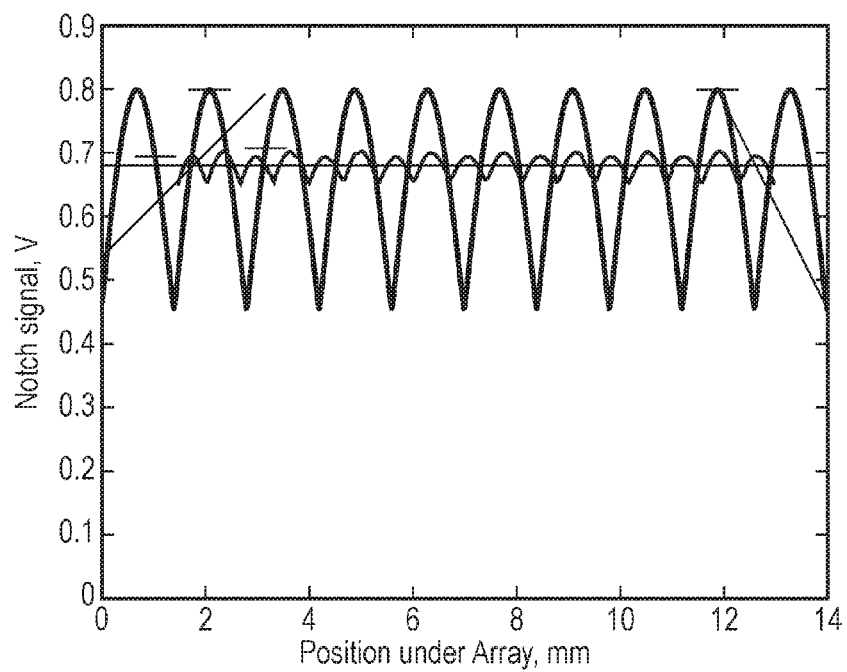
FIG. 7 is a graph showing a frequency response function of the eddy current array inspection device of FIG. 3.
Figure 8:
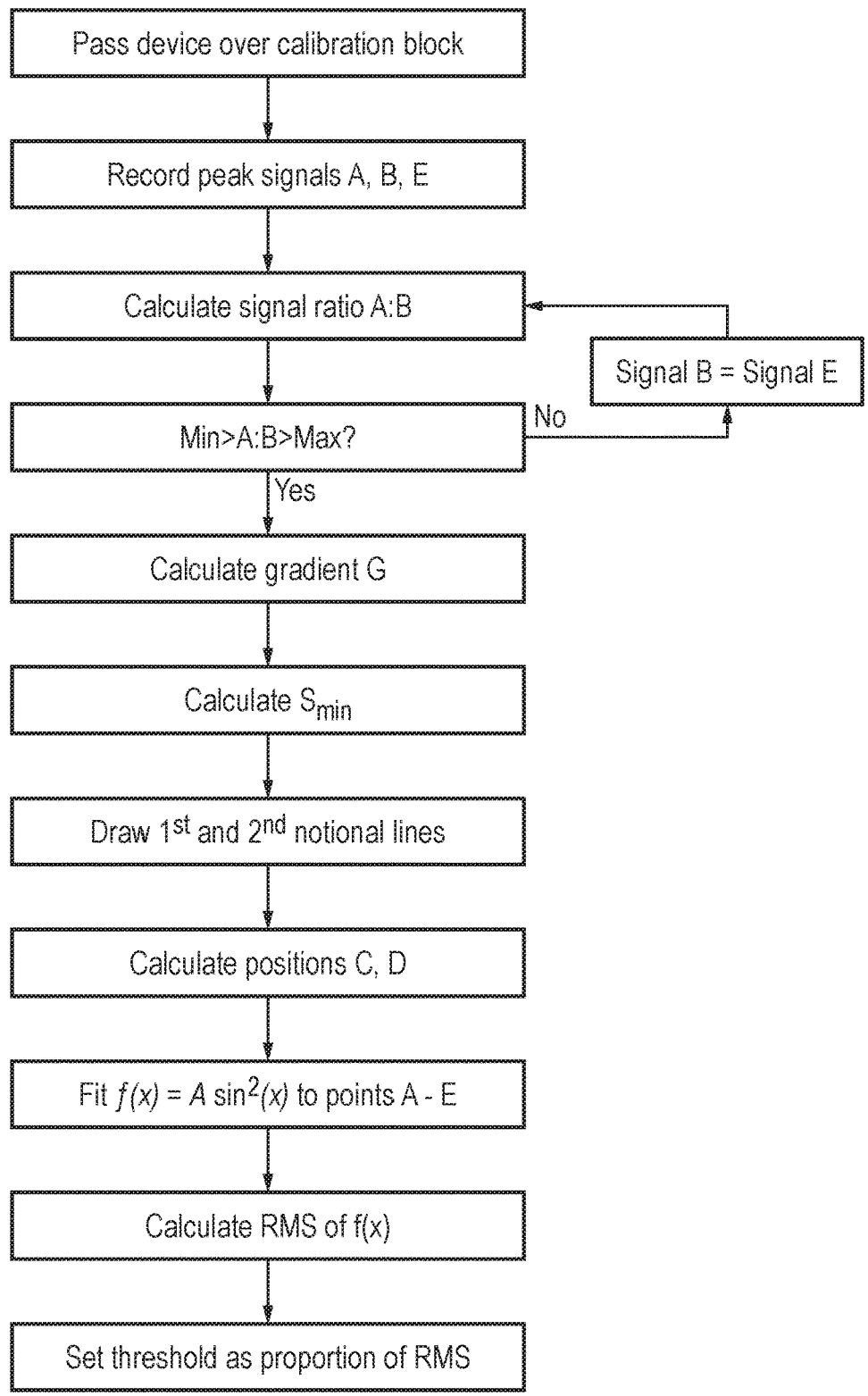
FIG. 8 is a flow diagram illustrating a second method of calibrating an eddy current array inspection device in accordance with the present disclosure.

FIG. 7 illustrates an alternative calibration method in accordance with the present disclosure. The array 102 is first normalised, as described above. In a first calibration step, the device 102 is passed over the calibrated defects 214, 216, 218, 220 in the same manner as in the first method. However, the subsequent signal processing steps differ from the first method.

In a second step, signals from adjacent sensor elements 112a, 112b are monitored as the device 102 traverses the defects 214-220. A peak sensor signal A, B from adjacent sensor elements 112a, 112b is measured, which is representative of elements passing defect 114. During the same pass, at least one further peak sensor signal E is measured from at least one further sensor 112e. Signals A, B are then compared, and a signal ratio A:B is calculated in a third step. As will be understood, if A=B, then the defect 114 is located at a point equidistant between the two sensors 112a, 112b, i.e. at the minimum of the array response function $x_{min}$, while if A is much greater than B (i.e. B is equal to the signal noise of the sensor 112), then the defect 114 is located at the maximum of the array response function, $x_{max}$. Consequently, the ratio A:B gives an estimate of the position of the defect 114 within the array function. In a fourth step therefore, the value of A:B is compared to a predetermined range of values. Provided the ratio of A:B is within the predetermined range of values, such that the defect is within a linear region of the array response function, the process can continue to the next step. Since a second calibrated defect 116 provided, spaced from the first defect 114 such that when the first defect is at the maximum of the array response function, the second is at the minimum, then at least one of these defects 114, 116 will be located at a position other than the array response function minimum $x_{min}$. In this case, if the ratio A:B is found to be outside the predetermined range for signals A, B from the first defect 114, then signal E is substituted for signal B, and the ratio A:B using this second defect 116 could be used. In some cases, a still further defect (not shown) could be provided, spaced from the other two defects 114, 116, and this signal could instead be substituted if the ratio A:B is outside the predetermined range.

In a fifth step, a gradient G is calculated from the signal ratio, by dividing the signal ratio A:B by the distance d between the adjacent sensors 112a, 112b.

In a sixth step, a signal amplitude $S_{min}$ at the array response function minimum at $x_{min}$ of the array response function is calculated by taking an average of the signals A and B, i.e. by applying the formula:

$$S_{min} = \frac{A+B}{2}$$

The position $x_{min}$ will be located at a position mid-way between signals A and B. The position in the x direction of signal A could be arbitrarily positioned at x=0, and the position of signal B is positioned at x=d, such that position $x_{min}$ is positioned at x=d/2.

In a seventh step, a first notional line extending from the minimum $x_{min}$ of the response function calculated in the sixth step and having the gradient G calculated in the fifth step is extrapolated. A second notional line extending from a position separated by half the channel width $\phi$ in the negative X direction, having the same magnitude as the gradient G, but with opposite sign (i.e. a reflection in the Y axis of gradient G). Points C and D are then defined lying along the notional line, having signal magnitudes corresponding to signals A and B respectively. A further point is generated by the position of point E, as measured by sensor 112$e$. The position in the Y axis is again determined by the sensor magnitude, and the position in the X axis by the distance between sensor 112$a$ and 112$e$.

In an eighth step, a candidate function of the form is fitted to the points A, B, C, D and E using a curve fitting algorithm, such as the Gauss-Newton method. In one example, the candidate function is of the form $f(x)=A\sin^2(x)$. In a second example, the candidate function comprises a series of overlapping Gaussian functions of the form:

$$f(x)=A\,e^{-((x-b)^2/2c^2)}$$

In an eighth step, an RMS of the resultant function is calculated. A rejection threshold is then set at a predetermined proportion of the RMS of the function in a ninth step.

The invention provides a method of calibrating an eddy current array inspection device with a high degree of accuracy using a single (or a small number) of calibration passes. Consequently, the calibration method can greatly reduce the setup time, and therefore cost, of an eddy current array inspection process. In particular, it has been found that the described calibration method may be used to accurately calibrate a sensor array where the required defect is less than half the distance between centres of adjacent sensors in the array in a single pass.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For example, the calibrated defects could comprise surface asperities, cavities, regions of different density, conductivity, permeability, or more generally, regions having a characteristic different to the surrounding region that the sensor is configured to detect. The sensor array could comprise dual coils, i.e. differentially-connected elements. The elements of the array could be arranged in a different pattern. For example, the rows could be staggered by ⅓ of the distance between elements of a row. Furthermore, the elements could have different shapes, such as ovals or polygons.

Aspects of any of the embodiments of the invention could be combined with aspects of other embodiments, where appropriate.

The invention claimed is:

1. A method of calibrating a sensor array comprising a plurality of sensor elements spaced from one another in a first direction, the calibration method comprising the following steps:
   providing a test workpiece comprising at least first and second calibrated defects spaced apart in the first direction by a characteristic distance such that, when the first calibrated defect is located at a position corresponding to a maximum of an array spatial response function defined by the array, the second calibrated defect is located at a position corresponding to a minimum of the array spatial response function;
   passing the array across the first and second calibrated defects in a direction normal to the first direction and determining a peak sensor signal from at least two of the sensor elements in the array to determine a root mean squared average of the array spatial response function; and
   setting a rejection threshold as a predetermined proportion of the root mean squared average of the array spatial response function.

2. A method according to claim 1, wherein the array comprises one of an eddy current sensor array, a Giant Magnetoresistance sensor array and a Hall Effect sensor array.

3. A method according to claim 1, wherein each of the first and second calibrated defects comprises an indentation in a surface of the test workpiece.

4. A method according to claim 1, wherein at least one of the first and second calibrated defects comprises a length in the first direction less than a channel width of the sensor elements.

5. A method according to claim 1, wherein the step of calculating the root mean squared of the array spatial response function comprises calculating an average of the determined peak sensor signals from a plurality of sensor elements in the array passing each of the calibrated defects.

6. A method according to claim 1, wherein the step of calculating the root mean squared average of the array spatial response function comprises:
   determining a ratio of peak sensor signals from adjacent sensor elements in the array when each passes over one of the calibrated defects, which is a first notch;
   determining a position of the first notch relative to the array spatial response function using the ratio of peak sensor signals;
   determining a first gradient by dividing the ratio by a channel width of the sensor elements;
   drawing first and second notional lines reflected about the first notch position, the first notional line having the first gradient and the second notional line having a magnitude of the first gradient and opposite sign;
   determining a plurality of candidate array spatial response function points having positions along the first and second notional lines;
   fitting a candidate function to the candidate array special response function points; and
   calculating a mean squared average of the candidate function.

7. A method according to claim 1, wherein the plurality of sensor elements are spaced from each other in the first direction by a constant channel width.

8. A method according to claim 7, wherein the first and second calibrated defects are separated from each other in the first direction by 1.5 times the channel width.

* * * * *